US012718941B2

(12) United States Patent
Bodurka et al.

(10) Patent No.: US 12,718,941 B2
(45) **Date of Patent: *Aug. 25, 2026**

(54) PATIENT SUPPORT APPARATUS AND MEDICAL DEVICE NETWORKS

(71) Applicant: Stryker Corporation, Kalamazoo, MI (US)

(72) Inventors: Alexander Josef Bodurka, Portage, MI (US); Krishna Sandeep Bhimavarapu, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 273 days.

This patent is subject to a terminal disclaimer.

(21) Appl. No.: 18/660,777

(22) Filed: May 10, 2024

(65) Prior Publication Data

US 2024/0296947 A1 Sep. 5, 2024

Related U.S. Application Data

(63) Continuation of application No. 17/559,339, filed on Dec. 22, 2021, now Pat. No. 11,984,221.

(Continued)

(51) Int. Cl.
*G16H 40/67* (2018.01)
*G16H 40/40* (2018.01)
(Continued)

(52) U.S. Cl.
CPC ............. *G16H 40/67* (2018.01); *G16H 40/40* (2018.01); *H04W 4/029* (2018.02); *H04W 4/33* (2018.02); *H04W 4/80* (2018.02)

(58) Field of Classification Search
CPC ......... G16H 40/67; G16H 40/40; H04W 4/33; H04W 4/029; H04W 4/80
See application file for complete search history.

(56) References Cited

U.S. PATENT DOCUMENTS 8,786,402 B2 * 7/2014 Barnes .................. G16H 40/40 340/5.1
9,838,836 B2 * 12/2017 Hayes .................. A61G 7/018

(Continued)

OTHER PUBLICATIONS

Hasan, Elsevier, 2019, pp. 178-198.*

*Primary Examiner* — Michael I Ezewoko
(74) *Attorney, Agent, or Firm* — Gardner, Linn, Burkhart & Ondersma LLP

(57) ABSTRACT

A system for automatically detecting medical devices positioned within a room of a healthcare facility includes a patient support apparatus, a headwall unit, and a controller. The patient support apparatus includes at least first and second transceivers and the headwall unit includes at least third and fourth transceivers. At least one of the first and second transceiver and at least one of the third and fourth transceivers are controller to determine first and second estimates of distance between the respective transceiver and a medical device. The controller uses the first and second estimates of distance to determine if the medical device is positioned within a threshold distance of the patient support apparatus and/or within a predetermined volume of space within the room. The transceivers used to determine the first and second estimates of distance may be Bluetooth Low Energy transceivers and/or ultra-wideband transceivers.

20 Claims, 5 Drawing Sheets

Related U.S. Application Data

(60) Provisional application No. 63/245,279, filed on Sep. 17, 2021, provisional application No. 63/245,245, filed on Sep. 17, 2021, provisional application No. 63/245,289, filed on Sep. 17, 2021, provisional application No. 63/193,777, filed on May 27, 2021, provisional application No. 63/161,175, filed on Mar. 15, 2021, provisional application No. 63/154,677, filed on Feb. 27, 2021, provisional application No. 63/132,514, filed on Dec. 31, 2020.

(51) Int. Cl.
*H04W 4/029* (2018.01)
*H04W 4/33* (2018.01)
*H04W 4/80* (2018.01)

(56) References Cited

U.S. PATENT DOCUMENTS 9,937,090 B2 * 4/2018 Hayes .................... G16H 40/20
10,016,325 B2 * 7/2018 Ribble ............... A61B 5/14552
10,085,905 B2 * 10/2018 Bhimavarapu .......... A61G 7/05
10,235,845 B2 * 3/2019 Bhimavarapu ........ G08B 5/228
10,290,071 B2 * 5/2019 Heil ....................... G16H 20/30
10,406,045 B2 * 9/2019 Hayes .................. A61G 1/0281
10,460,575 B2 * 10/2019 Bhimavarapu ...... A61G 7/0527
10,474,808 B2 * 11/2019 Huster .................... H04L 63/08
10,750,978 B2 * 8/2020 Bhimavarapu ....... A61B 5/1115
10,861,295 B2 * 12/2020 Bhimavarapu ...... A61B 5/7475
11,013,927 B2 * 5/2021 Hayes .................... G08B 25/08
11,031,130 B2 * 6/2021 Collins, Jr. ............ A61B 5/002
11,062,585 B2 * 7/2021 Durlach ............... A61G 7/0524
11,071,454 B2 * 7/2021 Bostic ...................... A61G 7/05
11,110,020 B2 * 9/2021 Bodurka ................. H04L 67/12
11,217,079 B2 * 1/2022 Mayoras, Jr. ........ A61B 5/7275
11,373,489 B2 * 6/2022 Bhimavarapu ...... A61G 7/0524
11,626,000 B2 * 4/2023 Durlach ............... A61G 7/0528
340/573.1
11,699,517 B2 * 7/2023 Receveur ............... G16H 40/20
705/2
11,830,336 B2 * 11/2023 Mayoras, Jr. ...... G08B 21/0453
11,869,649 B2 * 1/2024 Heil ..................... G06Q 10/063
11,984,221 B2 * 5/2024 Bodurka ................ G16H 40/67
12,023,286 B2 * 7/2024 Bodurka .................. A61G 7/05
12,144,770 B2 * 11/2024 Kebir ................... A61G 7/0506
2013/0253950 A1 * 9/2013 Vanderpohl, III ..... G16H 10/60
705/3
2013/0283529 A1 * 10/2013 Hayes .................... G16H 40/20
5/600
2014/0080413 A1 * 3/2014 Hayes .................... A61G 7/018
455/41.1
2014/0257849 A1 * 9/2014 Richards ................ G16H 40/67
705/3
2014/0297327 A1 * 10/2014 Heil ....................... G16H 40/40
700/282
2016/0038361 A1 * 2/2016 Bhimavarapu .... H04B 10/1149
2016/0140307 A1 * 5/2016 Brosnan ................. G06Q 10/10
600/509
2016/0367415 A1 * 12/2016 Hayes .................. A61G 1/0281
2017/0372025 A1 * 12/2017 Collins, Jr. ........... H04L 67/125
2018/0293849 A1 * 10/2018 Bhimavarapu ...... A61B 5/7475
2018/0296413 A1 * 10/2018 Ribble ................... A61B 5/208
2018/0296415 A1 * 10/2018 Seim .................... A61G 7/0524
2019/0172322 A1 * 6/2019 Bhimavarapu ....... A61B 5/1115
2019/0183705 A1 * 6/2019 Bodurka .................. H04B 5/48
2020/0050750 A1 * 2/2020 Heil ....................... G16H 20/17
2020/0051405 A1 * 2/2020 Bhimavarapu ........ G08B 5/228
2020/0090804 A1 * 3/2020 Robinson ............... G16H 40/40
2020/0118411 A1 * 4/2020 Wiggermann ..... G08B 21/0461
2020/0205661 A1 * 7/2020 Bostic .................... G16H 10/65
2020/0275877 A1 * 9/2020 Fitzgibbons .......... A61B 5/1115
2020/0312115 A1 * 10/2020 Durlach ................. G16H 40/20
2021/0049876 A1 * 2/2021 Bhimavarapu ....... A61B 5/1115
2021/0065885 A1 * 3/2021 Receveur ............... G16H 40/20
2021/0241904 A1 * 8/2021 Durlach ............... A61B 5/7435
2021/0393461 A1 * 12/2021 Bodurka .............. A61G 12/005
2022/0208318 A1 * 6/2022 Batman .................. G16H 40/63
2022/0208372 A1 * 6/2022 Bodurka ................ G16H 40/67
2023/0017210 A1 * 1/2023 Mayoras, Jr. .......... A61B 5/002
2023/0368645 A1 * 11/2023 Bhimavarapu ........ G16H 40/20
2024/0296947 A1 * 9/2024 Bodurka ................ G16H 40/67
2024/0350340 A1 * 10/2024 Bodurka ................ G16H 40/40
2025/0336509 A1 * 10/2025 Bhimavarapu ........ G16H 50/30

* cited by examiner

PATIENT SUPPORT APPARATUS AND MEDICAL DEVICE NETWORKS

CROSS-REFERENCE TO RELATED APPLICATIONS

This application claims priority to U.S. patent application Ser. No. 17/559,339 filed Dec. 22, 2021, by inventors Alexander Bodurka et al. and entitled PATIENT SUPPORT APPARATUS AND MEDICAL DEVICE NETWORKS, which in turn claims priority to the following commonly assigned U.S. provisional patent applications: U.S. provisional patent application Ser. No. 63/132,514 filed Dec. 31, 2020, by inventors Alexander Josef Bodurka et al., and entitled PATIENT SUPPORT APPARATUS AND MEDICAL DEVICE NETWORKS; U.S. provisional patent application Ser. No. 63/154,677 filed Feb. 27, 2021, by inventors Celso Pereira et al. and entitled SYSTEM FOR DETERMINING PATIENT SUPPORT APPARATUS AND MEDICAL DEVICE LOCATION; U.S. provisional patent application Ser. No. 63/161,175 filed Mar. 15, 2021, by inventors Krishna Bhimavarapu et al. and entitled EXERCISE DEVICE AND PATIENT SUPPORT APPARATUS; U.S. provisional patent application Ser. No. 63/193,777 filed May 27, 2021, by inventors Thomas Deeds et al. and entitled SYSTEM FOR ASSOCIATING MEDICAL DEVICE DATA; U.S. provisional patent application Ser. No. 63/245,245 filed Sep. 17, 2021, by inventors Kirby Neihouser et al. and entitled SYSTEM FOR LOCATING PATIENT SUPPORT APPARATUSES; U.S. provisional patent application Ser. No. 63/245,279 filed Sep. 17, 2021, by inventors Jerald Trepanier et al. and entitled PATIENT SUPPORT APPARATUSES WITH PATIENT MONITORING; and U.S. provisional patent application Ser. No. 63/245,289 filed Sep. 17, 2021, by inventors Madhu Thota et al. and entitled PATIENT SUPPORT APPARATUS COMMUNICATION AND LOCATION SYSTEM, the complete disclosures of all of which are incorporated herein by reference.

BACKGROUND

The present disclosure relates to patient support apparatuses, such as beds, cots, stretchers, recliners, or the like. More specifically, the present disclosure relates to a system for automatically determining the location of medical devices relative to a patient support apparatus and/or a defined volume of space within a room in which the medical device is positioned.

Existing hospital beds often include an exit detection system that detects when the patient leaves the bed and notifies a nurse call system that the patient has left the bed. Existing hospital beds also often include a nurse call button and speaker that allow the patient to communicate with a remote nurse using the nurse call system. Still other signals of the bed may also be communicated to and/or through the nurse call system, and/or to a room interface that routes the signals to one or more room devices. Such room devices may include a television, one or more lights, a thermostat, etc., and the signals communicated from the bed may include commands to change one or features of these devices (e.g. a volume or channel of the television, an on/off state of the television, a room temperature, etc.)

Medical devices are often used with a patient while the patient is positioned on a patient support apparatus. Those medical devices typically generate data regarding the patient that is forwarded to an electronic medical records server. In order for that data to be assigned to the medical records of the correct patient, one or more manual steps are typically required by a caregiver to associate the data from a particular medical device with a particular patient. In some cases, patient identity information is input into the medical device itself, and this identity information is transmitted with other data from the device to the EMR. This method requires that the transmitted patient data be properly secured against unauthorized disclosure so that unauthorized individuals do not gain access to the patient identify and his or her data. The present disclosure is directed to a system that overcomes past issues with associating data from medical devices with the medical records of the corresponding patient.

SUMMARY

According to various embodiments, the present disclosure is directed to a system that overcomes past issues with associating data from medical devices with the medical records of the corresponding patient. That is, the present disclosure provides a system and method for automatically establishing a wireless network of medical devices that are positioned within a threshold distance of a patient support apparatus and/or that are positioned within a predetermined volume of space defined within a room of a medical facility. In some embodiments, the location of the medical devices are automatically determined relative to a patient support apparatus and/or predetermined volume of space, and if the medical devices are within a threshold distance of the patient support apparatus and/or within the volume of space, the medical devices are automatically associated to the patient assigned to that patient support apparatus. Because neither the patient support apparatus nor the medical devices need to know the identity of the patient, the data transmitted from the patient support apparatus or the medical devices to a local server need not include any information that uniquely identifies the particular patient. Instead, the data may include a room and/or bay identifier, and a server that receives the data can use the room and/or bay identifier to correlate the data to a particular patient. Medical devices can therefore be automatically assigned to the correct patient without the need for caregivers to take any manual steps. Still other features and advantages of the present disclosure will be apparent to a person skilled in the art in light of the following written description and accompanying drawings.

According to one aspect of the present disclosure a system is provided for automatically detecting the presence of medical devices positioned within a room of a healthcare facility. The system includes a patient support apparatus, a headwall unit, and a controller. The patient support apparatus comprises a support surface adapted to support a person, a first transceiver adapted to establish a first wireless communication link with the headwall unit positioned at a fixed location in a room, and a second transceiver adapted to communicate a first set of wireless signals to and from a medical device separate from the patient support apparatus and the headwall unit. The first set of wireless signals is adapted to provide a first estimate of distance between the second transceiver and the medical device. The headwall unit comprises a third transceiver adapted to establish the first wireless communication link with the first transceiver of the patient support apparatus, and a fourth transceiver adapted to communicate a second set of wireless signals to and from the medical device. The second set of wireless signals is adapted to provide a second estimate of distance between the fourth transceiver and the medical device. The controller is adapted to process the first and second estimates to determine how far away the medical device is from at least one of the patient support apparatus or a volume of space defined within the room.

According to other aspects of the present disclosure, the controller is positioned inside one of the headwall unit or the patient support apparatus.

In some embodiments, at least one of the headwall unit or the patient support apparatus includes a network transceiver adapted to communicate with a local area network, and wherein the controller is positioned on a server in communication with the local area network.

In some embodiments, the headwall unit further comprises a fifth transceiver spaced away from the fourth transceiver a known distance. The fifth transceiver is adapted to communicate a third set of wireless signals to and from the medical device, wherein the third set of wireless signals is adapted to provide a third estimate of distance between the fifth transceiver and the medical device. In such embodiments, the controller is further adapted to process the third estimate with the first and second estimates to determine how far away the medical device is from the patient support apparatus and/or the volume of space.

In some embodiments, the patient support apparatus further comprises a fifth transceiver spaced away from the second transceiver a known distance. The fifth transceiver is adapted to communicate a third set of wireless signals to and from the medical device, wherein the third set of wireless signals adapted to provide a third estimate of distance between the fifth transceiver and the medical device. In such embodiments, the controller is further adapted to process the third estimate with the first and second estimates to determine how far away the medical device is from the patient support apparatus and/or the volume of space.

In some embodiments, the controller is in communication with an electronic memory in which is stored a length dimension of the patient support apparatus, a width dimension of the patient support apparatus, and a location of the second transceiver on the patient support apparatus relative to the length and width dimensions. In such embodiments, the controller is adapted to use the length dimension, the width dimension and the location of the second transceiver to determine how far away the medical device is from a boundary of the patient support apparatus, wherein the length and width dimensions define the boundary.

In some embodiments, the controller is adapted to determine an orientation of the patient support apparatus relative to the medical device.

In some embodiments, the second transceiver and fourth transceiver are ultra-wideband transceivers.

In some embodiments, the second and fourth transceivers are Bluetooth low energy transceivers.

In some embodiments, the controller is adapted to determine how far the medical device is from the patient support apparatus by using at least one of channel state information or angle of arrival information generated from the first and second sets of wireless signals.

The second transceiver and fourth transceiver, in some embodiments, include a first antenna array and a second antenna array, respectively.

In some embodiments, the controller is adapted to determine whether the medical device is able to join a network associated with the patient support apparatus based on whether the medical device is positioned within a threshold distance of the patient support apparatus or within the volume of space.

In some embodiments, the patient support apparatus further includes a second controller associated with the second transceiver and the headwall unit further includes a fourth controller associated with the fourth transceiver. In such embodiments, the controller may be adapted to determine whether the medical device is adapted to join the network based on votes received from the second and fourth controllers.

The controller, in some embodiments, is adapted to determine whether the medical device is able to join a network associated with a bay area of the room based on whether the medical device is currently positioned within the volume of space defined within the room.

The patient support apparatus, in some embodiments, is adapted to forward data received from the medical device to a server.

In some embodiments, the patient support apparatus is further adapted to forward location information indicating that the medical device is within at least one of a threshold distance to the patient support apparatus or within the volume of space defined within the room.

In some embodiments, the system further includes a second headwall unit positioned within the room, wherein the second headwall unit comprises a fifth transceiver adapted to communicate a third set of wireless signals to and from the medical device. The third set of wireless signals are adapted to provide a third estimate of distance between the fifth transceiver and the medical device, and the controller is further adapted to process the third estimate of distance with the first and second estimates to determine how far away the medical device is from at least one of the patient support apparatus or the volume of space defined within the room.

In some embodiments, the first and third transceivers are infrared transceivers.

In some embodiments, the second and fourth transceivers are ultra-wideband transceivers and the patient support apparatus further comprises a fifth transceiver adapted to communicate with a sixth transceiver positioned onboard the headwall unit. The fifth and sixth transceivers may be Bluetooth transceivers. In some embodiments, the fifth and sixth transceivers are further adapted to communicate third and fourth sets of wireless signals, respectively, to and from the medical device, wherein the third set of wireless signals is adapted to provide a third estimate of distance between the third transceiver and the medical device, and wherein the fourth set of wireless signals is adapted to provide a fourth estimate of distance between the fourth transceiver and the medical device. In such embodiments, the controller is further adapted to process the third and fourth estimates to determine how far away the medical device is from at least one of the patient support apparatus or the volume of space defined in the room.

In some embodiments, the volume of space encompasses a bay of the room.

In some embodiments, the headwall unit further includes a nurse call cable interface for connecting a nurse call cable between the headwall unit and a nurse call outlet of a nurse call system, and a headwall unit controller adapted to forward patient audio signals received from the patient support apparatus to the nurse call outlet.

In some embodiments, the headwall unit controller is further adapted to receive a volume control message from the patient support apparatus and to respond to the volume control message by sending a command to a television within the room to change its audio volume.

In any of the embodiments disclosed herein, the patient support apparatus may be one of a bed, a stretcher, a chair, a recliner, or a cot.

In any of the embodiments disclosed herein, additional transceivers may be positioned at known locations in the room of the healthcare facility and used to determine if the medical device is positioned within the threshold distance of the patient support apparatus and/or within the predetermined volume of space.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
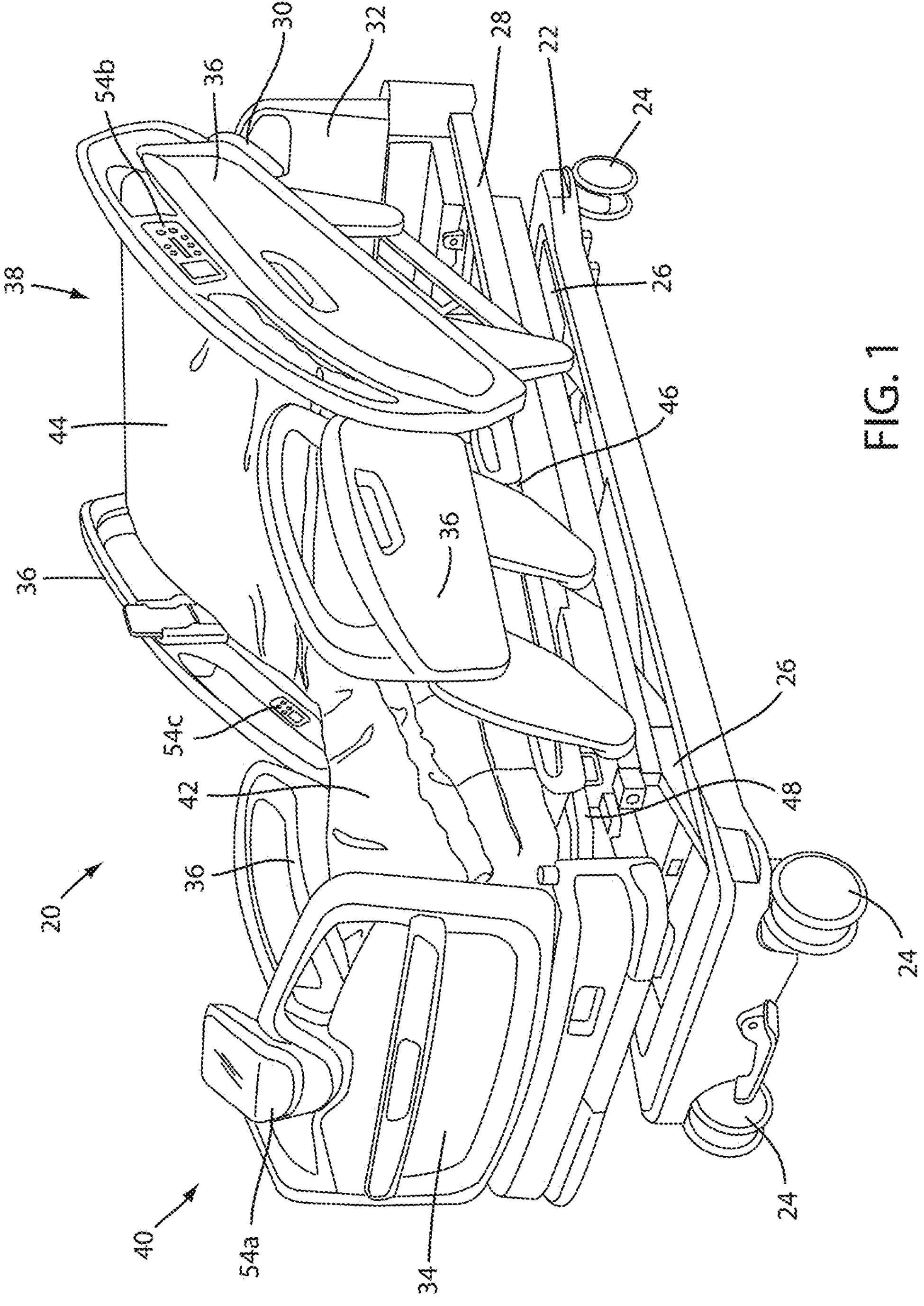
FIG. 1 is a perspective view of a patient support apparatus according to a first embodiment of the present disclosure.

An illustrative patient support apparatus 20 according to an embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a headboard 32, a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress 42, or other soft cushion, so that a person may lie and/or sit thereon. The top surface of the mattress 42 or other cushion forms a support surface for the occupant.

Support deck 30 is made of a plurality of sections, some of which are pivotable about generally horizontal pivot axes. In the embodiment shown in FIG. 1, support deck 30 includes at least a head section 44, a thigh section 46, and a foot section 48, all of which are positioned underneath mattress 42 and which generally form flat surfaces for supporting mattress 42. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some embodiments, patient support apparatus 20 may be modified from what is shown to include one or more components adapted to allow the user to extend the width of patient support deck 30, thereby allowing patient support apparatus 20 to accommodate patients of varying sizes. When so modified, the width of deck 30 may be adjusted sideways in any increments, for example between a first or minimum width, a second or intermediate width, and a third or expanded/maximum width.

As used herein, the term "longitudinal" refers to a direction parallel to an axis between the head end 38 and the foot end 40. The terms "transverse" or "lateral" refer to a direction perpendicular to the longitudinal direction and parallel to a surface on which the patient support apparatus 20 rests.

It will be understood by those skilled in the art that patient support apparatus 20 can be designed with other types of constructions, such as, but not limited to, that described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another embodiment, the construction of patient support apparatus 20 may include the same, or nearly the same, structures as the Model 3002 S3 bed manufactured and sold by Stryker Corporation of Kalamazoo, Michigan. This construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. In still another embodiment, the construction of patient support apparatus 20 may include the same, or nearly the same, structure as the Model 3009 Procuity MedSurg bed manufactured and sold by Stryker Corporation of Kalamazoo, Michigan. This construction is described in greater detail in the Stryker Maintenance Manual for the 3009 Procuity MedSurg bed (publication 3009-009-002, Rev. A.0), published in 2020 by Stryker Corporation of Kalamazoo, Michigan.

It will be understood by those skilled in the art that patient support apparatus 20 can be designed with still other types of constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The overall construction of patient support apparatus 20 may also take on still other forms different from what is disclosed in the aforementioned references provided the patient support apparatus includes the functions and features discussed in greater detail below.

Figure 2:
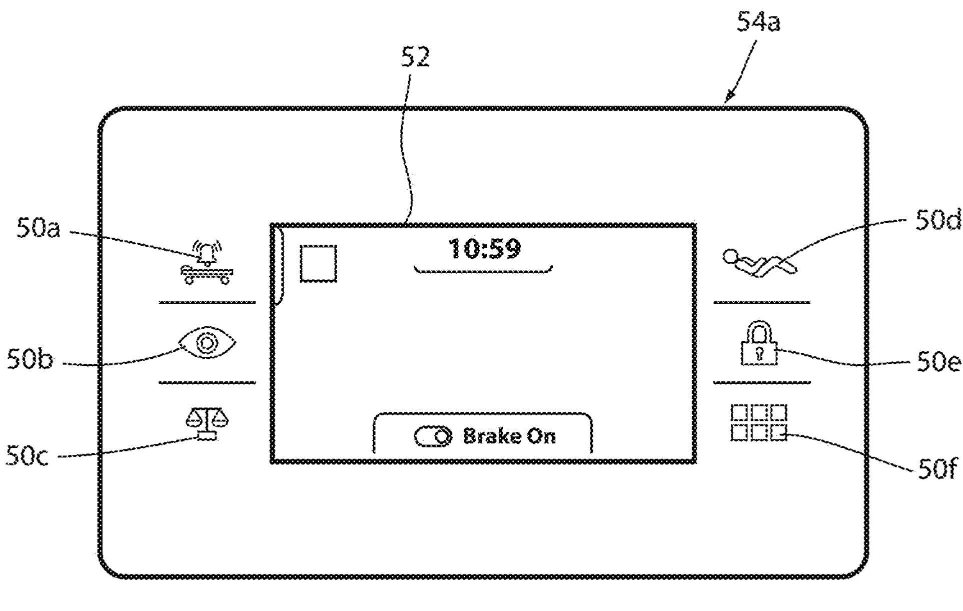
FIG. 2 is a plan view of an illustrative caregiver control panel of the patient support apparatus of FIG. 1.

Patient support apparatus 20 further includes a plurality of control panels 54 that enable a user of patient support apparatus 20, such as a patient and/or an associated caregiver, to control one or more aspects of patient support apparatus 20. In the embodiment shown in FIG. 1, patient support apparatus 20 includes a footboard control panel 54*a*, a pair of outer siderail control panels 54*b* (only one of which is visible), and a pair of inner siderail control panels 54*c* (only one of which is visible). Footboard control panel 54*a* and outer siderail control panels 54*b* are intended to be used by caregivers, or other authorized personnel, while inner siderail control panels 54*c* are intended to be used by the patient associated with patient support apparatus 20. Each of the control panels 54 includes a plurality of controls 50 (see, e.g. FIGS. 2-3), although each control panel 54 does not necessarily include the same controls and/or functionality.

Among other functions, controls 50 of control panel 54*a* allow a user to control one or more of the following: change a height of support deck 30, raise or lower head section 44, activate and deactivate a brake for wheels 24, arm and disarm an exit detection system and, as will be explained in greater detail below, communicate with the particular IT infrastructure installed in the healthcare facility in which patient support apparatus 20 is positioned. One or both of the inner siderail control panels 54*c* also include at least one control that enables a patient to call a remotely located nurse (or other caregiver). In addition to the nurse call control, one or both of the inner siderail control panels 54*c* also include one or more controls for controlling one or more features of one or more room devices positioned within the same room as the patient support apparatus 20. As will be described in more detail below, such room devices include, but are not necessarily limited to, a television, a reading light, and a room light. With respect to the television, the features that may be controllable by one or more controls 50 on control panel 54*c* include, but are not limited to, the volume, the channel, the closed-captioning, and/or the power state of the television. With respect to the room and/or night lights, the features that may be controlled by one or more controls 50 on control panel 54*c* include the on/off state and/or the brightness level of these lights.

Control panel 54*a* includes a display 52 (FIG. 2) configured to display a plurality of different screens thereon. Surrounding display 52 are a plurality of navigation controls 50*a-f* that, when activated, cause the display 52 to display different screens on display 52. More specifically, when a user presses navigation control 50*a*, control panel 54*a* displays an exit detection control screen on display 52 that includes one or more icons that, when touched, control an onboard exit detection system. The exit detection system is as adapted to issue an alert when a patient exit from patient support apparatus 20. Such an exit detection system may include any of the features and functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference.

When a user pressed navigation control 50*b* (FIG. 2), control panel 54 displays a monitoring control screen that includes a plurality of control icons that, when touched, control an onboard monitoring system built into patient support apparatus 20. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference.

When a user presses navigation control 50*c*, control panel 54*a* displays a scale control screen that includes a plurality of control icons that, when touched, control the scale system of patient support apparatus 20. Such a scale system may include any of the features and functions as, and/or may be constructed in any of the same manners as, the scale systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference.

When a user presses navigation control 50*d*, control panel 54 displays a motion control screen that includes a plurality of control icons that, when touched, control the movement of various components of patient support apparatus 20, such as, but not limited to, the height of litter frame 28 and the pivoting of head section 44. In some embodiments, the motion control screen displayed on display 52 in response to pressing control 50*d* may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference.

When a user presses navigation control 50*e*, control panel 54*a* displays a motion lock control screen that includes a plurality of control icons that, when touched, control one or more motion lockout functions of patient support apparatus 20. Such a motion lockout screen may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference.

When a user presses on navigation control 50*f*, control panel 54*a* displays a menu screen that includes a plurality of menu icons that, when touched, bring up one or more additional screens for controlling and/or viewing one or more other aspects of patient support apparatus 20. Such other aspects include, but are not limited to, diagnostic and/or service information for patient support apparatus 20, mattress control and/or status information, configuration settings, and other settings and/or information. One example of a suitable menu screen is the menu screen 100 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference.

For all of the navigation controls 50*a-f* (FIG. 2), screens other than the ones specifically mentioned above may be displayed on display 52 in other embodiments of patient support apparatus 20 in response to a user pressing these controls. Thus, it will be understood that the specific screens mentioned above are merely representative of the types of screens that are displayable on display 52 in response to a user pressing on one or more of navigation controls 50*a-f*. It will also be understood that, although navigation controls 50*a-f* have all been illustrated in the accompanying drawings as dedicated controls that are positioned adjacent display 52, any one or more of these controls 50*a-f* controls alternatively be touchscreen controls that are displayed at one or more locations on display 52. Still further, although controls 50*a-f* have been shown herein as buttons, it will be understood that any of controls 50*a-f* could also, or alternatively, be switches, dials, or other types of non-button controls.

Figure 3:
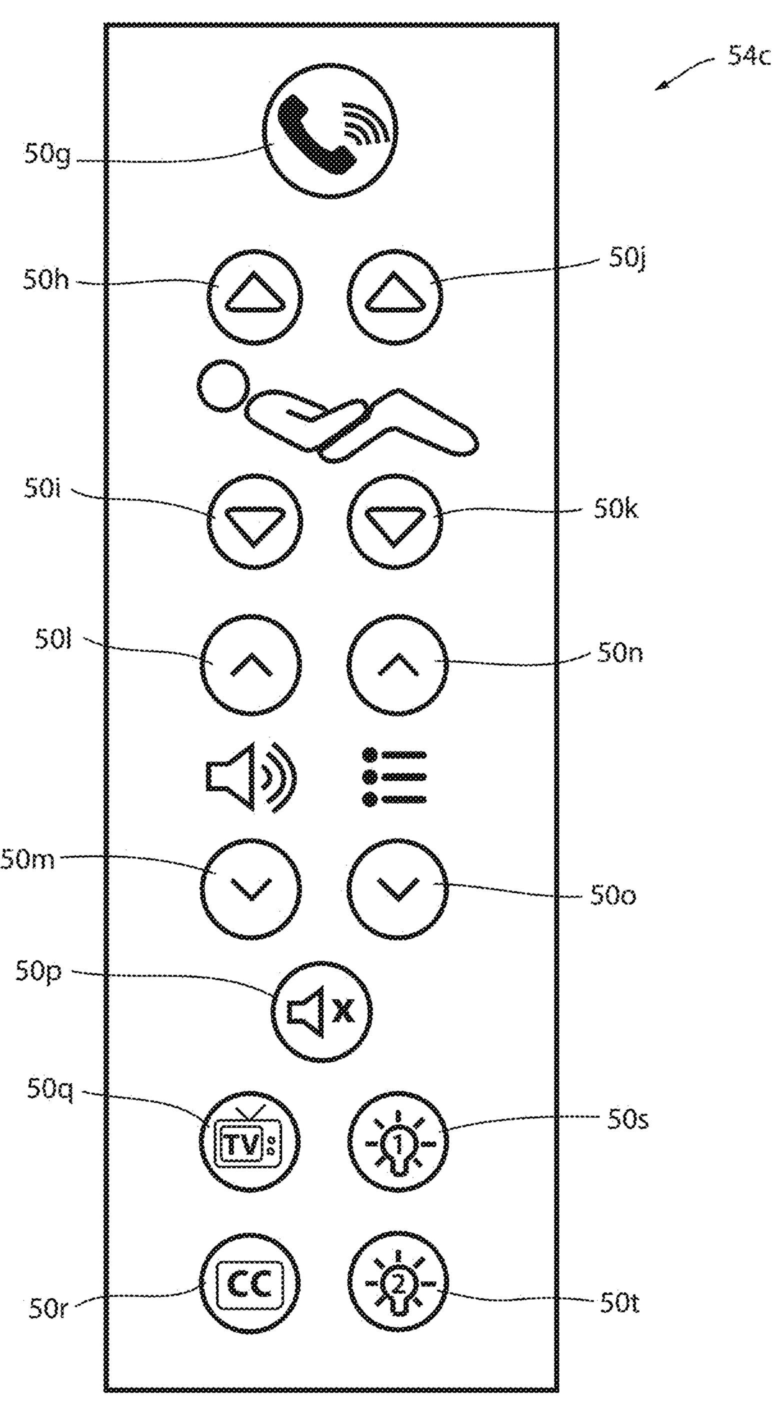
FIG. 3 is a plan view of an illustrative patient control panel of the patient support apparatus of FIG. 1.

FIG. 3 illustrates one example of a patient control panel 54*c* that may be incorporated into patient support apparatus 20 and positioned at a location on patient support apparatus 20 that is convenient for a patient to access while supported on support deck 30, such as on an interior side of one of the siderails 36. Control panel 54*c* includes a plurality of controls 50*g-t* that are intended to be operated by a patient. A nurse call control 50*g*, when pressed by the patient, sends a signal to a nurse call system requesting that a remotely positioned nurse talk to the patient. A Fowler-up control 50*h*, when pressed by the patient, causes a motorized actuator onboard patient support apparatus 20 to raise Fowler section 44 upwardly. A Fowler-down control 50*i*, when pressed by the patient, causes the motorized actuator to lower Fowler section 44 downwardly. A gatch-up control 50*j*, when pressed by the patient, causes another motorized actuator to raise a knee section of support deck 30, while a gatch-down control 50*k* causes the motorized actuator to lower the knee section of support deck 30.

A volume-up control 50*l*, when pressed by the patient, causes patient support apparatus 20 to send a signal to an in-room television instructing it to increase its volume, while a volume down control 50*m*, when pressed, causes patient support apparatus 20 to send a signal to the television instructing it to decrease its volume. A channel-up control 50*n*, when pressed by the patient, causes patient support apparatus 20 to send a signal to the television instructing it to increase the channel number, while a channel-down control 50*o*, when pressed, causes patient support apparatus 20 to send a signal to the television instructing it to decrease the channel number.

A mute control 50*p*, when pressed, causes patient support apparatus 20 to send a signal to the television instructing it to either mute itself or unmute itself, depending upon whether the television is currently muted or unmuted. In other words, mute control 50*p* is a toggle control that alternatingly sends mute and unmute commands to the television when it is pressed.

Power control 50*q* is a toggle control that, when pressed, sends a signal to the television to either turn on or turn off, depending upon the television's current power status. Closed-captioning control 50*r* is another toggle control that, when pressed, sends a signal to the television to either turn on its closed-captioning feature or to turn off its closed captioning feature, depending upon whether the closed-captioning feature is currently on or off.

Control 50*s* is a toggle control that, when pressed, sends a signal to a first light to either turn on or turn off, depending upon the current state of that first light. Control 50*t* is another toggle control that, when pressed, sends a signal to a second light to either turn on or turn off, depending upon the current state of that second light. In some embodiments, the first light is a reading light and the second light is a room light, both of which are positioned off-board the patient support apparatus 20.

It will be understood that not only the number of controls 50 on control panel 54*c*, but also the functions of the controls 50 on control panel 54*c*, the layout of the controls 50 on control panel 54*c*, and/or other aspects of control panel 54*c* may be modified from what is shown in FIG. 3. In some embodiments, control panel 54*c* is implemented on a pendant controller that includes a cable that is plugged into a port on patient support apparatus 20. Still other manners of implementing control panel 54*c* are also possible.

Figure 4:
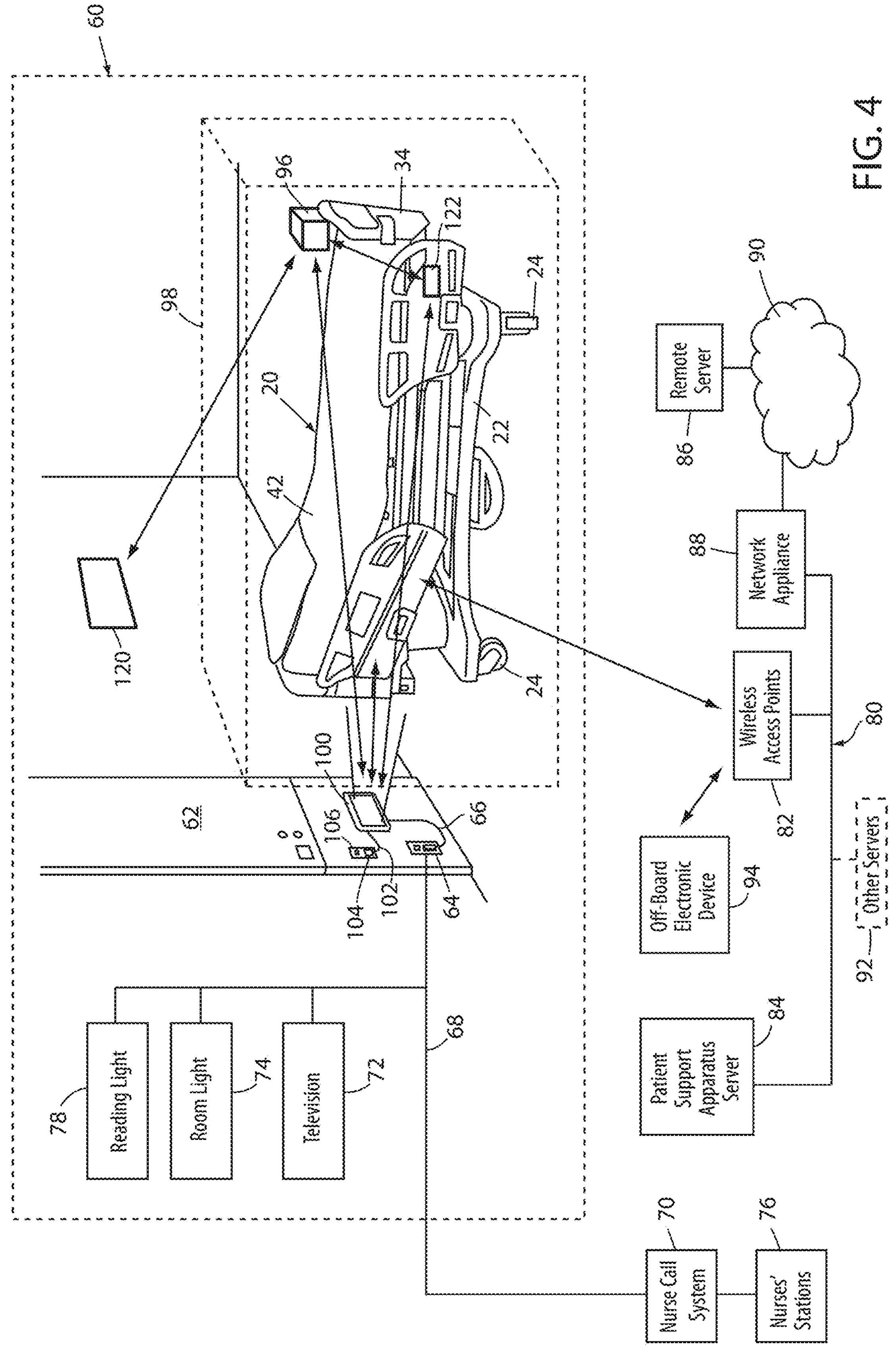
FIG. 4 is a diagram of a system for automatically detecting the position of medical devices positioned within a room of a healthcare facility.

FIG. 4 illustrates a system 108 for determining the location of one or more medical devices 96 relative to patient support apparatus 20 and/or a volume of space 98 defined within a room 60 of a conventional healthcare facility 56. System 108 includes patient support apparatus 20, one or more headwall units 100, one or more patient support apparatus location transceivers 122, and, in some embodiments, one or more fixed medical device locators 120. Fixed medical device locators 120 are positioned at known and fixed locations within the room 60. Patient support apparatus location transceivers 122 are built into patient support apparatus 20 and positioned therein at known locations on the body of patient support apparatus 20. As will be discussed in greater detail below, headwall unit(s) 100, fixed medical device locators 120, and patient support apparatus location transceivers 122 are adapted to determine if a medical device 96 is positioned within a threshold distance of patient support apparatus 20 and/or within the space volume 98. If so, the medical device is presumed to be associated with the patient assigned to that particular patient support apparatus 20.

As shown in FIG. 4, room 60 includes a headwall 62 into which a conventional communications outlet 64 is physically integrated. Communications outlet 64 is adapted to receive a nurse call cable 66 that physically connects at its other end either to patient support apparatus 20 (not shown) or to a wireless headwall unit 100 (shown in FIG. 4). As will be discussed in greater detail below, headwall unit 100 and nurse call cable 66 allow patient support apparatus 20 to communicate with a nurse call system, and one or more room devices positioned within room 60.

Communication outlet 64 is electrically coupled to one or more cables or other conductors 68 that electrically couple the communication outlet 64 to a nurse call system 70 and one or more room devices, such as a television 72, a room light 74, and/or a reading light 78. Conductors 68 are typically located behind headwall 62 and not visible. In some healthcare facilities, conductors 68 may first couple to a room interface circuit board that includes one or more conductors 68 for electrically coupling the room interface circuit board to room devices 72, 74, 78 and/or nurse call system 70. Still other communicative arrangements for coupling communication outlet 64 to nurse call system 70 and/or one or more room devices 72, 74, 78 are possible.

Room devices 72, 74, 78 are conventional room devices that are typically present in a conventional hospital room. In most cases, the particular brand and model of the television 72 and/or lights 74, 78 will vary from healthcare facility to healthcare facility, and may vary from room to room within the same healthcare facility. The different models and/or brands of televisions 72, room lights 74, and/or reading lights 78 are often controlled in different manners. For example, the signals that are input into a first brand of television in order to change a channel may require a first voltage level, while the signals that are input into a second brand of television in order to change the channel may require a second voltage level. Still further, apart from differences in voltage levels, the sequence of bits and/or other information that is sent to a television to change the channel, for example, may vary from brand to brand, or from model to model. Still other aspects of the control of the television 72 and/or lights 74, 78 may vary from brand to brand and/or from model to model. Thus, in order for a patient to properly control the television 72 and/or lights 74, 78 using one of the patient control panels 54*c*, patient support apparatus 20 or headwall unit 100 need to be properly configured to match the particular television 72 and/or lights 74, 78 that are positioned in the same room as the patient support apparatus 20.

Returning to FIG. 4, nurse call cable 66 enables patient support apparatus 20 to communicate with nurse call system 70 and/or room devices 72, 74, 78. A patient supported on patient support apparatus 20 who activates a nurse call control (e.g. 50*g*; see FIG. 3) on patient support apparatus 20 causes a signal to be wirelessly sent from patient support apparatus 20 to headwall unit 100, which in turn conveys the signal via nurse call cable 66 to the nurse call system 70, which forwards the signal to a one or more remotely located nurses (e.g. nurses at one or more nurses' stations 76). If the patient activates one or more room device controls (e.g. controls 501-*t*; see FIG. 3), one or more wireless signals are conveyed to headwall unit 66, which in turn sends appropriate signals via nurse call cable 66 to communication outlet 64 and the room devices 72, 74, 78 that change one or more features of these devices (e.g. the volume, channel, on/off state, etc.).

As is also shown in FIG. 4, patient support apparatus 20 is further configured to communicate with a local area network 80 of the healthcare facility 56. In the embodiment shown in FIG. 4, patient support apparatus 20 includes a wireless network transceiver 126 (FIG. 5) that communicates wirelessly with local area network 80. It will be understood, however, that in some embodiments, patient support apparatus 20 is adapted to communicate with network 80 via a wired connection, such as an Ethernet cable that plugs into an Ethernet port (e.g. an RJ-45 style port, an 8P8C port, etc.) built into patient support apparatus 20. In other embodiments, patient support apparatus 20 includes a wireless network transceiver, such as, but not limited to, a WiFi transceiver (e.g. IEEE 802.11) that wirelessly communicates with one or more wireless access points 82 of local area network 80. In still other embodiments, patient support apparatus 20 includes both a wired port for communicating with network 80 via a wired connection and a wireless connection for communicating with network 80.

Patient support apparatus 20 is configured to communicate with one or more servers on local area network 80 of healthcare facility 56. One such server is a patient support apparatus server 84. Patient support apparatus server 84 is adapted, in at least one embodiment, to receive status information from patient support apparatuses 20 positioned within healthcare facility 56 and distribute this status information to caregivers, other servers, and/or other software applications. In some embodiments, patient support apparatus server 84 is configured to communicate at least some of the status data received from patient support apparatuses 20 to a remote server 86 that is positioned geographically remotely from healthcare facility 56. Such communication may take place via a network appliance 88, such as, but not limited to, a router and/or a gateway, that is coupled to the Internet 90. The remote server 86, in turn, is also coupled to the Internet 90, and patient support apparatus server 84 is provided with the URL and/or other information necessary to communicate with remote server 86 via the Internet connection between network 80 and server 86.

As will be discussed in greater detail below, patient support apparatus server 84 may also carry out additional functions, such as, but not limited to, determining the location of one or more medical devices 96 positioned within room 60. Depending upon whether the location of the medical device 96 is within a volume of space 98 defined within the room, and/or within a threshold distance of patient support apparatus 20, patient support apparatus server 84 may be configured to determine whether to allow the medical device 96 to join a wireless network that is associated with the patient assigned to patient support apparatus 20 or not. When joined to the network, the data from the medical device 96 is automatically associated with the patient assigned to patient support apparatus 20. In some embodiments, all or a portion of this location determination, network control, and/or patient-device association is carried out by server 84. In other embodiments, one or more of these functions may be partially or wholly carried out by controllers onboard patient support apparatus 20 and/or onboard headwall unit 100.

It will be understood that the architecture and content of local area network 80 will vary from healthcare facility to healthcare facility, and that the example shown in FIG. 4 is merely one example of the type of network a healthcare facility may be employ. Typically, additional servers 92 will be hosted on network 80 and one or more of them may be adapted to communicate with patient support apparatus server 84. For example, an electronic health record server will typically be present in any healthcare facility, and in some embodiments discussed herein will be in communication with patient support apparatus server 84 in order to receive patient data that is to be recorded in a patient's health record (e.g. weight readings taken from the scales built into patient support apparatuses 20; therapies provided to patients using a powered mattress 42 onboard patient support apparatuses 20, data from a medical device 96 that is determined to be associated with the patient assigned to patient support apparatus 20, etc.). Local area network 80 will also typically allow one or more electronic devices 94 to access the local area network 80 via wireless access points 82. Such electronic devices 94 include, but are not limited to, smart phones, tablet computers, portable laptops, desktop computers, and other types of electronic devices that include a WiFi capability and that are provided with the proper credentials (e.g. SSID, password, etc.) to access network 80.

Headwall units 100 are adapted to wirelessly receive signals from patient support apparatus 20 and deliver the signals to communications outlet 64 in a manner that matches the way the signals would otherwise be delivered to communications outlet 64 if a conventional nurse call cable 66 were connected directly between patient support apparatus 20 and communications outlet 64. In other words, patient support apparatus 20 and headwall unit 100 cooperate to provide signals to communications outlet 64 in a manner that is transparent to communications outlet 64 such that outlet 64 cannot detect whether it is in communication with patient support apparatus 20 via a wired connection or it is in communication with patient support apparatus 20 via a wireless connection between patient support apparatus 20 and headwall unit 100 (the latter of which is in wired communication with outlet 64). In this manner, a healthcare facility can utilize the wireless communication abilities of one or more patient support apparatuses 20 without having to make any changes to their existing communication outlets 64.

In addition to sending signals received from patient support apparatus 20 to communications outlet 64, headwall units 100 are also adapted to forward signals received from communications outlet 64 to patient support apparatus 20. Headwall units 100 are therefore adapted to provide bidirectional communication between patient support apparatus 20 and communications outlet 64. Such communication includes, but is not limited to, communicating command signals from any of controls 50 and/or from any of electronic device 94 to corresponding room devices 72, 74, and/or 78. Such communication also includes communicating audio signals between a person supported on patient support apparatus 20 and a caregiver positioned remotely from patient support apparatus 20. The audio signals received by headwall units 100 from a microphone on patient support apparatus 20 are forwarded to communications outlet 64, and the audio signals received from communications outlet 64 are forwarded to a speaker onboard patient support apparatus 20.

Nurse call cable 66, in some embodiments, includes a conventional 37 pin connector on each end, one of which is adapted to be inserted into outlet 64 and the other one of which is adapted to be inserted into headwall unit 100. Such 37 pin connections are one of the most common types of connectors found on existing headwalls of medical facilities for making connections to the nurse call system 70 and room devices 72, 74, and 78. Headwall unit 100 and nurse call cable 66 are therefore configured to mate with one of the most common type of communication outlets 64 used in medical facilities. Such 37 pin connectors, however, are not the only type of connectors, and it will be understood that headwall unit 100 can utilize different types of connectors that are adapted to electrically couple to different types of nurse call cables 66 and/or different types of communication outlets 64. One example of such an alternative communications outlet 64 and cable is disclosed in commonly assigned U.S. patent application Ser. No. 14/819,844 filed Aug. 6, 2015 by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of communication outlets 64 and corresponding connectors may be utilized.

Headwall unit 100 (FIG. 4) also includes an electrical cord 102 having a plug 104 positioned at a far end that is adapted to be inserted into a conventional electrical outlet 106. Electrical cord 102 enables headwall unit 100 to receive power from the mains electrical supply via outlet 106. It will be appreciated that, in some embodiments, headwall unit 100 is battery operated and cord 102 be omitted. In still other embodiments, headwall unit 100 may be both battery operated and cord 102 so that in the event of a power failure, battery power supplies power to headwall unit 100, and/or in the event of a battery failure, electrical power is received through outlet 106.

In addition to any of the structures and functions described herein, headwall units 100 may be configured to communicate location data to patient support apparatus 20 that enables patient support apparatus 20 and/or patient support apparatus server 84 to determine the location of patient support apparatus 20 within healthcare facility 56. Such location determination may be carried out in any of the manners disclosed in commonly assigned U.S. Pat. No. 9,999,375 issued Jun. 19, 2018, to inventors Michael Hayes et al. and entitled LOCATION DETECTION SYSTEMS AND METHODS, the complete disclosure of which is incorporated herein by reference.

Headwall units 100 may also perform additional functions. In some embodiments, headwall units 100 may perform any of the functions performed by the headwall units 76 disclosed in commonly assigned U.S. patent application Ser. No. 16/215,911 filed Dec. 11, 2018, by inventors Alexander Bodurka et al. and entitled HOSPITAL HEADWALL COMMUNICATION SYSTEM, the complete disclosure of which is incorporated herein by reference. In some embodiments, headwall units 100 may also, or alternatively, perform any of the same functions performed by the headwall interfaces 72 disclosed in commonly assigned U.S. patent application Ser. No. 16/193,150 filed Nov. 16, 2018, by inventors Alexander Bodurka et al. and entitled PATIENT SUPPORT APPARATUSES WITH LOCATION/MOVEMENT DETECTION, the complete disclosure of which is also incorporated herein by reference. In still other embodiments, headwall units 100 may also, or alternatively, perform any of the same functions performed by the headwall units 66 disclosed in commonly assigned U.S. patent application Ser. No. 16/217,203 filed Dec. 12, 2018, by inventor Alexander Bodurka et al. and entitled SMART HOSPITAL HEADWALL SYSTEM, the complete disclosure of which is incorporated herein by reference.

In some embodiments, headwall units 100 may be constructed to include any or all of the functionality of the wireless headwall units disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference.

In some embodiments, headwall units 100 may also be constructed to include any or all of the functionality of the headwall units disclosed in commonly assigned U.S. patent application Ser. No. 63/026,937 filed May 19, 2020, by inventors Alexander Bodurka et al. and entitled PATIENT SUPPORT APPARATUSES WITH HEADWALL COMMUNICATION, the complete disclosure of which is also incorporated herein by reference.

Still further, in some embodiments, patient support apparatus 20 and/or patient support apparatus server 84 may include any or all of the functionality of the patient support apparatuses and/or patient support apparatus servers described in any of the aforementioned commonly assigned U.S. patents and/or patent applications.

Figure 5:
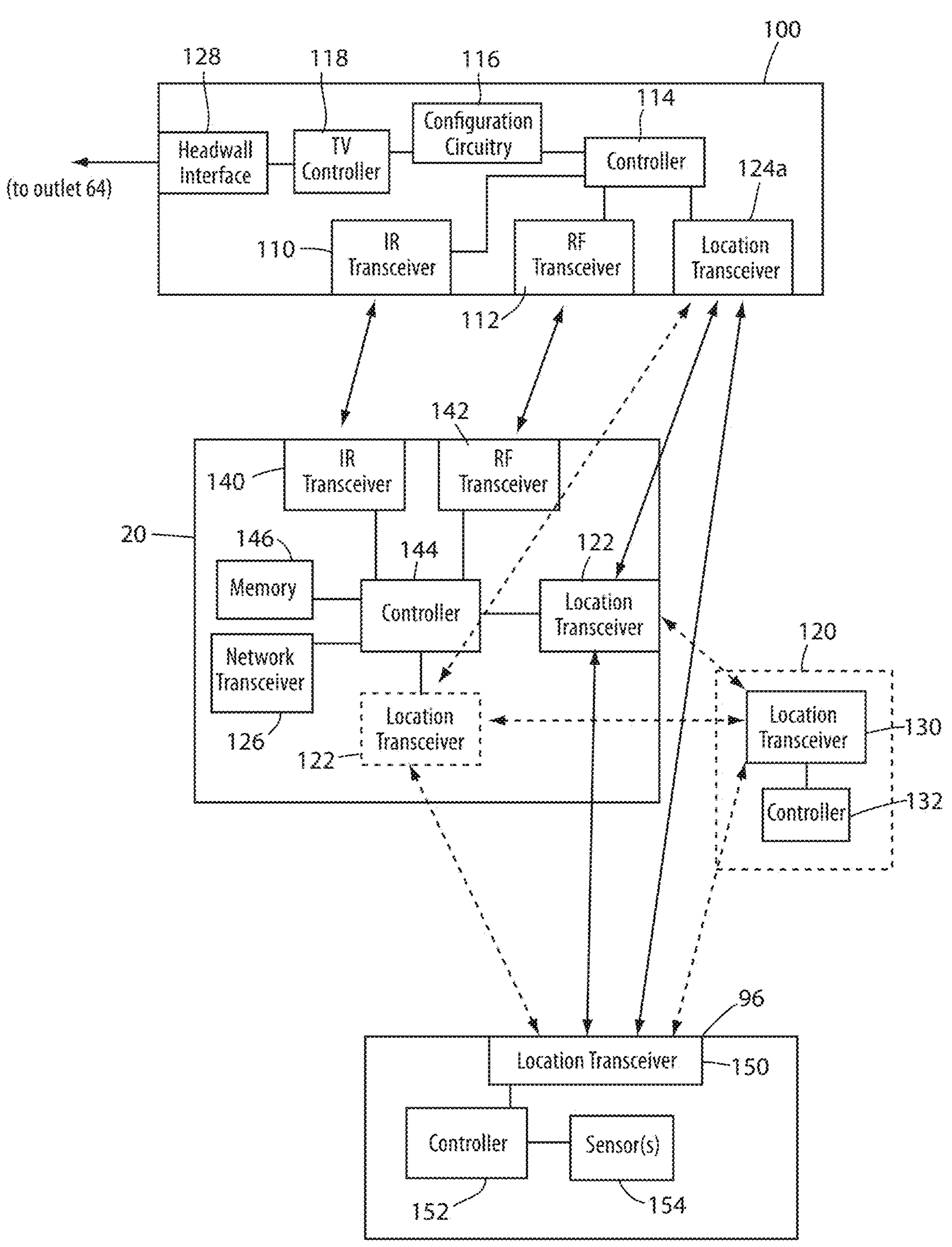
FIG. 5 is a block diagram of several components of the system of FIG. 4.

FIG. 5 depicts in block diagram various components of system 108. These include patient support apparatus 20, headwall unit 100, a fixed medical device locator 120, and a medical device 96. It will be understood that the components depicted in FIG. 5 are not necessarily a complete set of components, and that system 108 may additionally include one or more additional fixed medical device locators 120. Further, it will be understood that internal circuitry of each of these components may include more than what is shown in FIG. 5. For example, while headwall unit 100 is depicted in FIG. 5 to include only a single location transceiver, it will be understood that it may include more than one of these. Similarly, although patient support apparatus 20 is depicted as include one location transceiver and one optional location transceiver, it may include more than these. Still other variations are possible.

As was noted, system 108 is adapted to determine if one or more medical devices 96 are positioned within a threshold range of patient support apparatus 20 or within a predefined volume of space 98 (FIG. 4). The predefined volume of space may be defined in a fixed manner relative to the dimensions of the room 60 (and thus stationary), or it may be defined relative to patient support apparatus 20 (and thus moveable). When defined in fixed manner, volume 98 will typically include the space defined by a particular bay within the room 60. That is, it will encompass the volume typically occupied by the patient support apparatus 20 when the patient support apparatus 20 is in its customary position within the room 60. It will also typically encompass the space surrounding the customary position of the patient support apparatus 20 in which medical devices 96 that may be used with the patient on patient support apparatus 20. Although FIG. 4 depicts volume 98 as a generally rectangular volume, it will be understood that this is merely one example of the shape that volume 98 may take on. Other non-rectangular shapes and/or shapes having rectangular portions may be used with system 108. Volume 98 generally corresponds to the volume of space in which a medical device must be positioned in order to be admitted to a patient support apparatus communication network that includes patient support apparatus 20.

Headwall unit 100 (FIG. 5) includes an infrared transceiver 110, a Bluetooth transceiver 112, a headwall unit controller 114, configuration circuitry 116, smart television control circuitry 118, and a headwall interface 128. Headwall unit 100 also includes at least one location transceiver **126*a* that is used in conjunction with other location transceivers 124 to determine the location of medical device 96. Infrared transceiver 110 is adapted to communicate with infrared transceiver 140 of patient support apparatus 20 using infrared waves. Bluetooth transceiver 112 is adapted to communicate with Bluetooth transceiver 142 of patient support apparatus 20 using RF waves in accordance with the conventional Bluetooth standard (e.g. IEEE 802.14.1 and/or the standard maintained by the Bluetooth Special Interest Group (SIG) of Kirkland, Washington, USA. In some embodiments, transceivers 112 and 142** utilized Bluetooth Low Energy communications.

Headwall unit controller 114 is adapted to control the operation of transceivers 110, 112, configuration circuitry 116, TV controller 118, headwall interface 128, and location transceiver **124*a*. Headwall controller 114 and location transceiver 124*a* together define an "anchor point." In some embodiments, location transceiver 124*a* is an ultra-wideband transceiver. In other embodiments, location transceiver 124*a* is a Bluetooth Low Energy transceiver. In still other embodiments, location transceiver 124*a* may be combined with RF transceiver 112 such that it is used both to communicate with patient support apparatus 20 and to determine a distance between itself and medical device 96. Location transceiver 124*a*, as with all of the location transceivers discussed herein, may include an array of antennas that are used to assist in the determination of location. Controller 114 of headwall unit 100 uses location transceiver 124*a* to determine the distance between headwall unit 100 and medical device 96, as well as, in some embodiments, the distances between one or more location transceivers 122 positioned onboard patient support apparatus 20 and headwall unit 100**.

Patient support apparatus 20 includes a controller 144, a memory 146, and the transceivers 140, 142, 126, and 122 mentioned above. Network transceiver 126 may be a WiFi transceiver, or other type of transceiver, that is adapted to communicate with local area network 80. Each location transceiver 122 above patient support apparatus 20 is positioned at a known location on patient support apparatus 20. This known location may be stored in memory 146 and/or elsewhere. Controller 144 utilizes location transceivers 122 to determine distances between each transceiver 122 and medical device 96. These distances may be determined utilizing Angle of Arrival (AoA) information, Channel State Information, time-of-flight information, time-difference-of-arrival, and/or information about signals passed between these transceivers and a transceiver aboard medical device 96.

Fixed locator 120 also includes a location transceiver 130 and a controller 132. Controller 132, like controller 144 of patient support apparatus 20, controls location transceiver 130 to determine the distance between locator 120 and medical device 96. This distance may be determined using time-of-flight measurements, time-difference of arrival measurements, angle-of-attack measurements, and/or other measurements that enable a relative position to be determined.

Medical device 96 includes a location transceiver 150, controller 152, and, in some instances, one or more sensors 154 that gather data regarding the patient assigned to patient support apparatus 20. Controller 152, like controllers 114, 144, and 132, controls location transceiver 150 to determine the distance between locator medical device 96 and the other location transceivers **124*a*, 130, and 122 positioned within the room 60**. These distances may be determined in the same manners mentioned above.

Each location transceiver **124*a*, 122, 130, and 150 are, in at least one embodiment, ultra-wideband transceivers that are adapted to determine the aforementioned distances using time of flight and/or other characteristics of the signals exchanged between themselves. In another embodiment, each of these transceivers 124*a*, 122, 130, and 150 are Bluetooth Low Energy transceivers that are adapted to determine the distances between themselves using angle of arrival and/or channel state information. In some embodiments, each location transceiver 124*a*, 122, 130, and/or 150** are implemented as any of the Trimension™ ultra-wideband modules available from NXP Semiconductors of Austin, Texas. These modules include, but are not limited to, the Trimension™ UWB modules ASMOP1BOON1, ASMOP1CO0R1, and/or the ASMOP1CO0A1, that utilize any of the following chips: the NXP SR150, SR100T, SR040, NCJ29D5, and/or the OL23DO chips. Modules manufactured and/or marketed by other companies may also be used, including, but not limited to, the Decawave DWM1000, DWM10001C, DWM3000 modules (available from Decawave of Dublin, Ireland); the Nordic TSG5162 SiP module (available from Tsingoal Technology of Beijing, China); and/or the UWB hub, wand, and/or sensors available from Zebra technologies of Lincolnshire, Illinois. Still other types of UWB modules may be used to implement these location transceivers.

From the aforementioned distances, as well as the knowledge of the position of fixed headwall unit 100 and fixed locators 120 relative to the volume of defined space 98, one or more controllers are able to determine the position of medical device 96 relative to the defined space 98. The one or more controllers may include any one or more of controller 114, 144, 132, and/or 152, and/or it may include, as noted above, a controller integrated into server 84 (or another server). Alternatively, or additionally, from aforementioned known position information, as well as the known position of transceivers 122 onboard patient support apparatus 20, one or more controllers are able to determine the position of medical device 96 relative to patient support apparatus 20. This relative position information may include data stored in memory 146, or elsewhere, regarding the dimensions of patient support apparatus 20. Further, the one or more controllers may also determine, in some embodiments, the orientation of patient support apparatus 20 relative to medical device 96. Each of the location transceivers **124*a*, 122, 130, and 150, and their associated controller 114, 144, 132, and 152**, define an "anchor point." Thus, each of these anchor points may include an array of antennas.

One or more of the controllers 114, 144, or 132 may control whether or not medical device 96 is allowed to join the patient support apparatus communication network based on the aforementioned distances. It will be understood that, in some alternative embodiments, the network may be defined based upon proximity to a patient support apparatus 20, rather than proximity to a particular bay within a healthcare facility. The determination of whether a medical device 96 is able to join one of these networks is carried out in any of the manners described in the Appendix to U.S. provisional patent application Ser. No. 63/132,514 filed Dec. 31, 2020, by inventors Alexander Josef Bodurka et al., and entitled PATIENT SUPPORT APPARATUS AND MEDICAL DEVICE NETWORKS, the complete disclosure of which has already been incorporated herein by reference.

Once a medical device is part of the patient support apparatus network, that medical device is determined to be associated with the patient assigned to patient support apparatus 20. Further, in some embodiments, data from the medical device 96 is routed through one or more components of the network (e.g. patient support apparatus 20, headwall unit 100, or fixed locator 120), and these components assign a non-patient specific identifier to the data. The non-patient specific identifier, in some embodiments, corresponds to the particular patient support apparatus 20 or the specific headwall unit 100. Server 84, or another server of network 80, includes a data structure that correlates the specific bays within the healthcare facility and/or the specific patient support apparatuses 20 to particular patients. The server 84 can therefore correlate the data from the medical device 96 to a particular patient and route it to the electronic medical records system with the information necessary to have it stored in the matching records of the patient assigned to patient support apparatus 20. Thus, charting of data from medical devices 96 can be carried out automatically.

Each of controllers 114, 144, 132, and 152 may take on a variety of different forms. In the illustrated embodiment, each of these controllers is implemented as a conventional microcontroller. However, these controllers may be modified to use a variety of other types of circuits-either alone or in combination with one or more microcontrollers-such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 114, 144, 132, and 152 when carrying out the functions described herein, as well as the data necessary for carrying out these functions, are stored in a corresponding memory that is accessible to that particular controller 114, 144, 132, and 152.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A unit positioned at a fixed location within a room of a healthcare facility and adapted to wirelessly communicate with a patient support apparatus, the unit comprising:

a first ultra-wideband (UWB) transceiver adapted to establish a first wireless communication link with a second UWB transceiver onboard the patient support apparatus;

a first radio frequency (RF) transceiver adapted to communicate establish a second wireless communication link with a second RF transceiver onboard the patient support apparatus;

an interface adapted to communicate with a communication outlet communicatively coupled to a nurse call system; and a controller adapted to use the first UWB transceiver to determine a first distance between the first UWB transceiver and the second UWB transceiver, to use the first UWB transceiver to determine a second distance between the first UWB transceiver and a third UWB transceiver onboard a device separate from the patient support apparatus, to forward audio signals received by the first RF transceiver from the second RF transceiver to the interface, to automatically associate data from the device with a patient assigned to the patient support apparatus if the second distance is less than a threshold distance, and to not associate data from the device with the patient assigned to the patient support apparatus if the second distance is greater than the threshold.

2. The unit of claim 1 wherein the controller is further adapted to use the second distance to determine whether the device is allowed to join a network.

3. The unit of claim 1 wherein the controller is further adapted to forward audio signals received from the communication outlet to the second RF transceiver onboard the patient support apparatus.

4. The unit of claim 1 further comprising a fourth UWB transceiver adapted to establish a third wireless link with the second UWB transceiver onboard the patient support apparatus, and wherein the controller is further adapted to use the fourth UWB transceiver to determine a third distance between the fourth UWB transceiver and the second UWB transceiver.

5. The unit of claim 1 wherein the first UWB transceiver is further adapted to establish a third wireless communication link with a fourth UWB transceiver positioned onboard the patient support apparatus, and to use the first UWB transceiver to determine a third distance between the first UWB transceiver and the fourth UWB transceiver.

6. The unit of claim 1 further comprising a fourth UWB transceiver adapted to establish a third wireless link with the third UWB transceiver onboard the device, and wherein the controller is further adapted to use the fourth UWB transceiver to determine a third distance between the fourth UWB transceiver and the third UWB transceiver.

7. The unit of claim 1 wherein the first UWB transceiver is further adapted to establish a third wireless communication link with a fourth UWB transceiver positioned onboard the device, and to use the first UWB transceiver to determine a third distance between the first UWB transceiver and the fourth UWB transceiver.

8. The unit of claim 1 wherein the controller is further adapted to use at least one of the first or second distances to determine how far away the device is from at least one of the following: (a) the patient support apparatus, or (2) a volume of space defined within the room.

9. The unit of claim 1 wherein the controller is further adapted to transmit location data to the patient support apparatus and the location data indicates a location of the patient support apparatus within the healthcare facility.

10. The unit of claim 1 wherein the device is a medical device and the controller is adapted to allow the medical device to join a network if the second distance is less than a threshold distance.

11. A patient support apparatus comprising:

a support surface adapted to support a person;

a first ultra-wideband (UWB) transceiver adapted to establish a first wireless communication link with a second UWB transceiver onboard a unit positioned at a fixed location within a room of a healthcare facility;

a first radio frequency (RF) transceiver adapted to communicate establish a second wireless communication link with a second RF transceiver onboard the unit; and a controller adapted to use the first UWB transceiver to determine a first distance between the first UWB transceiver and the second UWB transceiver, to use the first UWB transceiver to determine a second distance between the first UWB transceiver and a third UWB transceiver onboard a device separate from the patient support apparatus and the unit, and to determine whether the second distance is less than a threshold distance, to automatically associate data from the device with a patient assigned to the patient support apparatus if the second distance is less than a threshold distance, and to not associate data from the device with the patient assigned to the patient support apparatus if the second distance is greater than the threshold.

12. The patient support apparatus of claim 11 wherein the controller is further adapted to forward audio signals from a microphone onboard the patient support apparatus to the unit using the first RF transceiver.

13. The patient support apparatus of claim 11 further comprising a fourth UWB transceiver onboard the patient support apparatus and adapted to establish a third wireless link with the third UWB transceiver onboard the device, and wherein the controller is further adapted to use the fourth UWB transceiver to determine a third distance between the fourth UWB transceiver and the third UWB transceiver.

14. The patient support apparatus of claim 11 wherein the first UWB transceiver is further adapted to establish a third wireless communication link with a fourth UWB transceiver positioned onboard the unit, and to use the first UWB transceiver to determine a third distance between the first UWB transceiver and the fourth UWB transceiver.

15. The patient support apparatus of claim 11 further comprising a fourth UWB transceiver onboard the patient support apparatus and adapted to establish a third wireless link with the second UWB transceiver onboard the unit, and wherein the controller is further adapted to use the fourth UWB transceiver to determine a third distance between the fourth UWB transceiver and the second UWB transceiver.

16. The patient support apparatus of claim 11 wherein the first UWB transceiver is further adapted to establish a third wireless communication link with a fourth UWB transceiver positioned onboard the device, and to use the first UWB transceiver to determine a third distance between the first UWB transceiver and the fourth UWB transceiver.

17. The patient support apparatus of claim 11 wherein the controller is further adapted to use at least one of the first or second distances to determine how far away the device is from at least one of the following: (a) the patient support apparatus, or (2) a volume of space defined within the room.

18. The patient support apparatus of claim 11 wherein the controller is further adapted to receive location data from the unit and the location data indicates a location of the patient support apparatus within the healthcare facility.

19. The patient support apparatus of claim 11 wherein the device is a medical device, and the controller is adapted to allow the medical device to join a network if the second distance is less than a threshold distance.

20. The patient support apparatus of claim 11 further comprising a network transceiver adapted to communicate with a local area network of the healthcare facility, wherein the controller is adapted to forward data from the device to the local area network if the second distance is less than a threshold distance.

* * * * *